US011020593B2

(12) United States Patent
Brown

(10) Patent No.: US 11,020,593 B2
(45) Date of Patent: *Jun. 1, 2021

(54) SYSTEM AND METHOD FOR ENHANCING THE BINAURAL REPRESENTATION FOR HEARING-IMPAIRED SUBJECTS

(71) Applicants: UNIVERSITY OF PITTSBURGH-OF THE COMMONWEALTH SYSTEM OF HIGHER EDUCATION, Pittsburgh, PA (US); ARIZONA BOARD OF REGENTS ACTING FOR AND ON BEHALF OF ARIZONA STATE UNIVERSITY, Scottsdale, AZ (US)

(72) Inventor: Christopher A. Brown, Pittsburgh, PA (US)

(73) Assignees: University of Pittsburgh-Of the Commonwealth System of Higher Education, Pittsburgh, PA (US); Arizona Board of Regents Acting for and on Behalf of Arizona State University, Scottsdale, AZ (US)

( * ) Notice: Subject to any disclaimer, the term of this patent is extended or adjusted under 35 U.S.C. 154(b) by 141 days.

This patent is subject to a terminal disclaimer.

(21) Appl. No.: 15/211,173

(22) Filed: Jul. 15, 2016

(65) Prior Publication Data

US 2016/0330551 A1 Nov. 10, 2016

Related U.S. Application Data

(63) Continuation of application No. 14/170,870, filed on Feb. 3, 2014, now Pat. No. 9,407,999.

(Continued)

(51) Int. Cl.
*A61N 1/36* (2006.01)
*H04R 25/00* (2006.01)

(52) U.S. Cl.
CPC ......... *A61N 1/36038* (2017.08); *H04R 25/43* (2013.01); *H04R 25/505* (2013.01); *H04R 25/552* (2013.01); *H04R 2430/03* (2013.01); *H04S 2420/01* (2013.01); *H04S 2420/07* (2013.01)

(58) Field of Classification Search
None
See application file for complete search history.

(56) References Cited

U.S. PATENT DOCUMENTS 6,850,496 B1   2/2005   Knappe et al.
8,503,704 B2   8/2013   Francart et al.
(Continued)

*Primary Examiner* — Qin Zhu
(74) *Attorney, Agent, or Firm* — Philip E. Levy; Eckert Seamans Cherin & Mellott, LLC

(57) ABSTRACT

A method of enhancing binaural representation for a subject includes receiving a first signal and a second signal in response to a plurality of sound sources, generating a number of estimated interaural time differences using the first signal and the second signal, converting each of the number of estimated interaural time differences to a corresponding interaural level difference, using one or more of the corresponding interaural level differences to generate an adjusted first signal, and using the adjusted first signal to generate a number of signals delivered to the subject for enhancing the hearing of the subject.

23 Claims, 3 Drawing Sheets

Related U.S. Application Data

(60) Provisional application No. 61/760,401, filed on Feb. 4, 2013.

(56) References Cited

U.S. PATENT DOCUMENTS

| | | |
|---|---|---|
| 2004/0196994 A1 | 10/2004 | Kates |
| 2007/0140506 A1 | 6/2007 | Roeck et al. |
| 2008/0019548 A1 | 1/2008 | Avendano |
| 2009/0304203 A1 | 12/2009 | Haykin et al. |
| 2010/0111338 A1 | 5/2010 | Ypma et al. |
| 2011/0280424 A1 | 11/2011 | Takagi et al. |
| 2012/0008807 A1 | 1/2012 | Gran |
| 2012/0093329 A1* | 4/2012 | Francart ............ A61N 1/36032 381/60 |
| 2012/0099733 A1 | 4/2012 | Wang et al. |
| 2013/0195296 A1 | 8/2013 | Merks |
| 2013/0322669 A1 | 12/2013 | Boretzki et al. |
| 2014/0010373 A1 | 1/2014 | Gran et al. |
| 2014/0193009 A1 | 7/2014 | Yousefian Jazi et al. |

* cited by examiner

SYSTEM AND METHOD FOR ENHANCING THE BINAURAL REPRESENTATION FOR HEARING-IMPAIRED SUBJECTS

CROSS-REFERENCE TO RELATED APPLICATIONS

This application is a continuation of U.S. patent application Ser. No. 14/170,870, filed on Feb. 3, 2014, entitled "SYSTEM AND METHOD FOR ENHANCING THE BINAURAL REPRESENTATION FOR HEARING-IMPAIRED SUBJECTS," which claims priority under 35 USC § 119(e) from U.S. Provisional Patent Application No. 61/760,401, filed on Feb. 4, 2013, the contents of which are incorporated herein by reference.

GOVERNMENT CONTRACT

This invention was made with government support under grant #DC008329 awarded by the National Institutes of Health. The government has certain rights in the invention.

BACKGROUND OF THE INVENTION

1. Field of the Invention

The present invention pertains to systems and methods for enhancing the hearing of hearing-impaired subjects, and in particular, in the exemplary embodiment to a system and method for enhancing the binaural representation for hearing-impaired subjects.

2. Description of the Related Art

There are two main binaural cues for localizing sound in the plane of azimuth, namely (i) interaural time differences (ITDs), and (ii) interaural level differences (ILDs). ILDs are a high-frequency cue, and occur because a sound that is off to one side of a listener's head is louder at the near ear than it is at the far ear (see FIG. 1 discussed herein). ITDs are a low-frequency cue, and are comprised of very small differences in the time-of-arrival between the two ears when a sound is off to one side.

An auditory environment containing one or more sound sources (talkers or other sources of sound) is often referred to as an auditory scene. Individuals with normal hearing can use the binaural cues discussed above for sound localization to improve speech intelligibility in an auditory scene where one talker (referred to as a target) and a second talker (referred to as a masker) are spatially separated from one another, such as in the well-known "cocktail-party" problem. Such an improvement in speech intelligibility is referred to in the art as a spatial release from masking (SRM).

Although listeners with hearing impairment can often understand speech in quiet settings as well as listeners with normal hearing, they often show dramatic declines in speech understanding in the presence of background noise. A competing talker is often the most challenging type of background noise, and is also the most difficult to ameliorate with typical noise-reduction schemes. More specifically, individuals with hearing impairment show little SRM. As a result, these listeners are less able to make sense of an auditory scene that contains multiple sound sources, and are thus typically unable to understand speech in the presence of noise, such as another talker.

A cochlear implant (CI) is a surgically implanted electronic device that provides a sense of sound to a person having a hearing impairment. In some people, cochlear implants can enable sufficient hearing for better understanding of speech. The quality of sound is different from natural hearing, with less sound information being received and processed by the brain. However, many patients are able to hear and understand speech and environmental sounds.

Implanting both cochleas of hearing-impaired listeners with cochlear implants (referred to as bilateral cochlear implants (BCIs)) has become more common in recent years. However, implantation is invasive, costly, and can potentially destroy any residual hearing in the ear to be implanted. A loss of residual hearing can be detrimental to speech reception, even if the amount of hearing is extremely limited. Thus, it is crucial that clear benefits of BCIs over a single device, with or without the addition of residual hearing, be established to justify the decision to implant the second ear. One often-cited potential outcome of BCI is the ability of such users to perceive and use binaural cues. However, BCI users have thus far shown relatively poor localization abilities and limited SRM. This is likely because BCI users receive limited access to binaural cues. First, they perceive only ILDs and not ITDs. Second, as shown in FIG. 1, robust ILDs are generally restricted to frequencies above about 1500-2000 Hz because the longer wavelengths at lower frequencies are not shadowed by the head. Thus, the binaural representation of BCI users is inconsistent across frequency, and it has been shown that sensitivity to binaural cues declines with such an inconsistency. In addition, any ILDs that BCI users receive will be subjected to large amounts of compression in the processing electronics of the BCIs. This includes automatic gain control on the processing frontend, which essentially limits the level of more intense sounds, likely reducing ILDs as a result, and the compression that occurs to map the input dynamic range (which is typically 60 dB or less) to the electric dynamic range (typically 10-20 dB).

There is thus a need for an effective system and method for enhancing the binaural representation for hearing-impaired subjects, such as, without limitation, those subject that have BCIs.

SUMMARY OF THE INVENTION

In one embodiment, a method of enhancing binaural representation for a subject is provided that includes receiving a first signal and a second signal in response to a plurality of sound sources, generating a number of estimated interaural time differences using the first signal and the second signal, converting each of the number of estimated interaural time differences to a corresponding interaural level difference, using one or more of the corresponding interaural level differences to generate an adjusted first signal, and using the adjusted first signal to generate a number of signals delivered to the subject for enhancing the hearing of the subject.

DETAILED DESCRIPTION OF EXEMPLARY EMBODIMENTS

Figure 1:
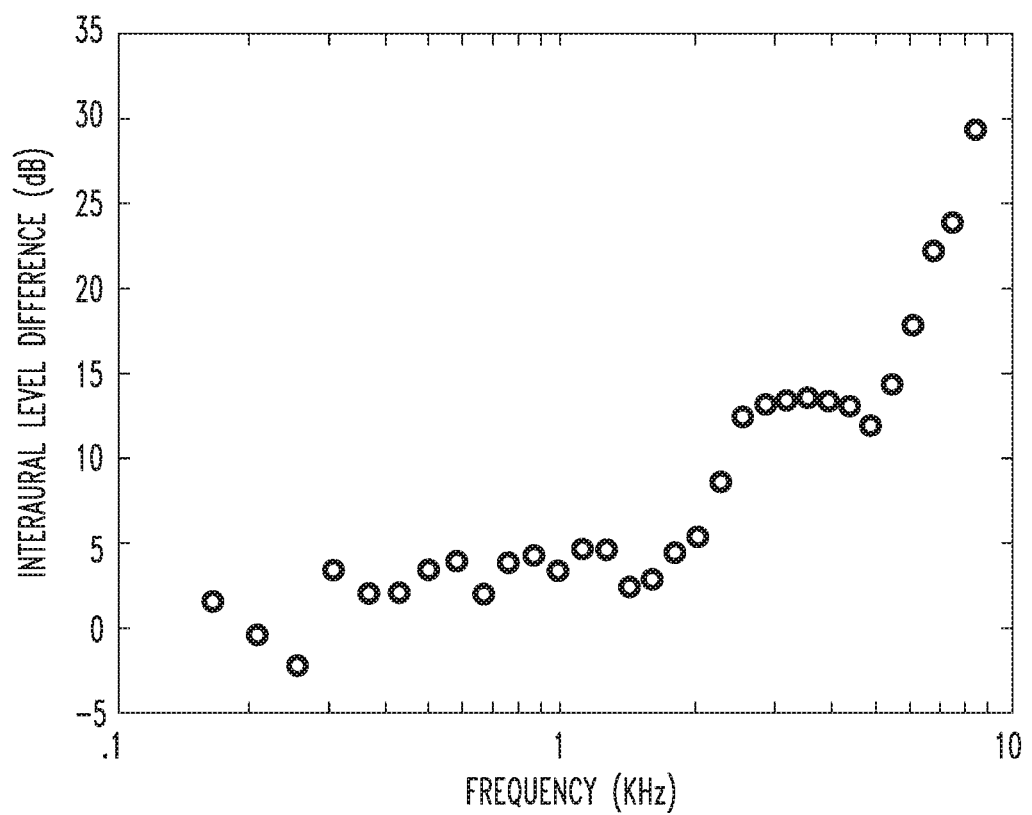
FIG. 1 is a graph plotting ILDs versus frequency in the prior art.

As used herein, the singular form of "a", "an", and "the" include plural references unless the context clearly dictates otherwise.

As used herein, the statement that two or more parts or elements are "coupled" shall mean that the parts are joined or operate together either directly or indirectly, i.e., through one or more intermediate parts or elements, so long as a link occurs.

As used herein, "directly coupled" means that two elements are directly in contact with each other.

As used herein, "fixedly coupled" or "fixed" means that two elements are coupled so as to move as one while maintaining a constant orientation relative to each other.

As used herein, the word "unitary" means a part is created as a single piece or unit. That is, a part that includes pieces that are created separately and then coupled together as a unit is not a "unitary" part or body.

As employed herein, the statement that two or more parts or elements "engage" one another shall mean that the parts exert a force against one another either directly or through one or more intermediate parts or elements.

As employed herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a routine, a thread of execution, a program, and/or a computer.

As used herein, the term "hearing enhancement device" shall refer to any electronic or electroacoustic device structured to enhanced the hearing of a user, and shall include, without limitation, cochlear implants and hearing aids.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
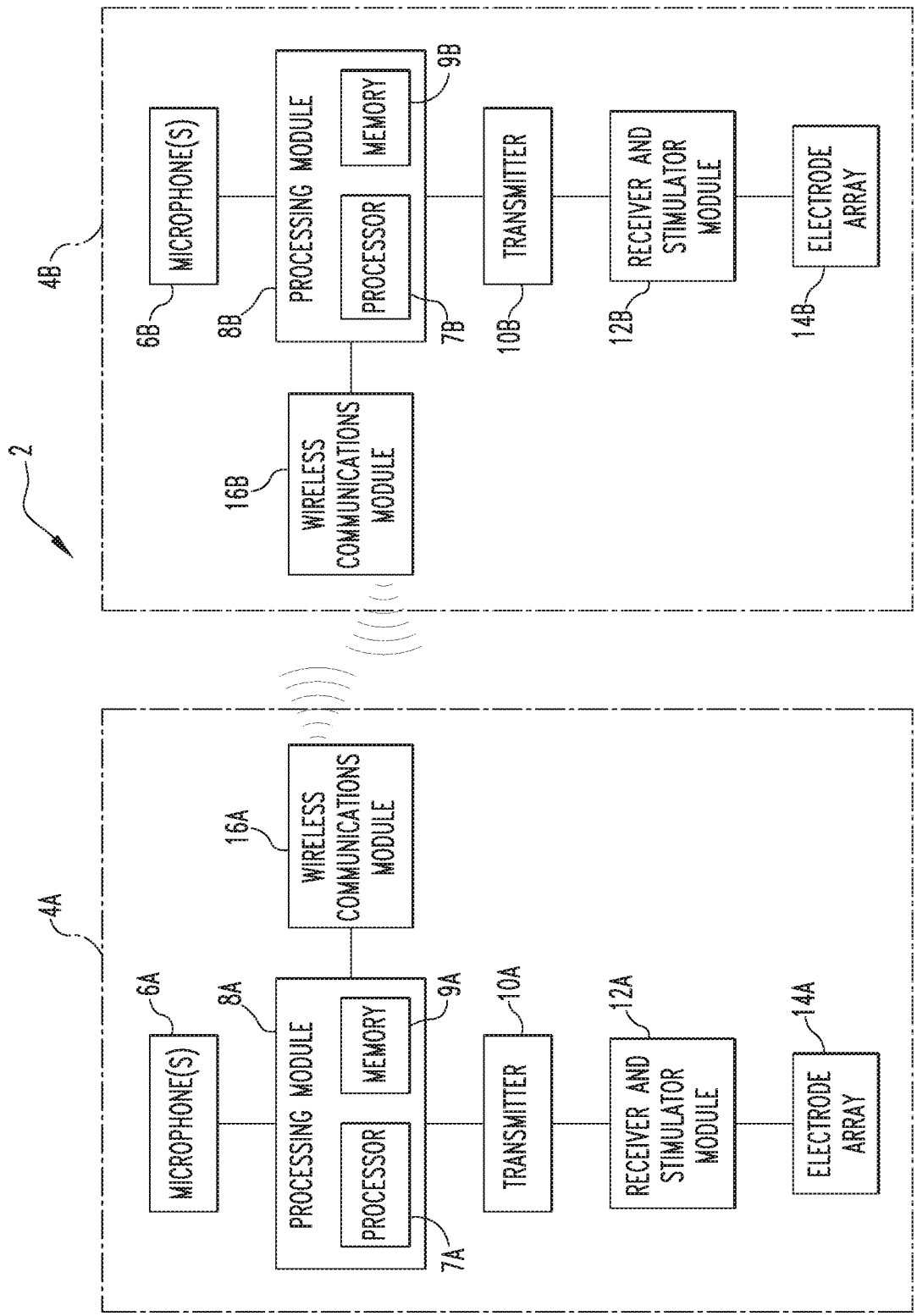
FIG. 2 is a schematic diagram of a system for enhancing the binaural representation for hearing-impaired subjects according to one exemplary, non-limiting embodiment of the disclosed concept.

FIG. 2 is a schematic diagram of a system 2 for enhancing the binaural representation for hearing-impaired subjects according to one exemplary, non-limiting embodiment of the disclosed concept. System 2 is a BCI system of a subject that includes a first cochlear implant 4A associated with the first (e.g., left) ear of the subject and a second cochlear implant 4B associated with the second (e.g., right) ear of the subject. As described in greater detail herein, system 2 of the present exemplary embodiment is structured to enhance the binaural representation for the subject in order to improve the signal to noise ratio (SNR) for the subject by estimating ITDs and converting those ITDs to ILDs.

As seen in FIG. 2, cochlear implant 4A includes one or more microphones 6A which are structured to pick up sound (such as from one or more talkers) from the environment surrounding system 2 and generate an electronic signal representing the sound. Microphone(s) 6A is coupled to a processing module 8A. Processing module 8A comprises a processor 7A and a memory 9A. Processor 7A may be, for example and without limitation, a microprocessor (µP), a microcontroller, or some other suitable processing device, that interfaces with memory 9A. Memory 9A can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 9A has stored therein a number of routines that are executable by processor 7A for processing the signals generated by microphone(s) 6A in order to produce the signals that are needed to communicate sound to the subject. One or more of the routines implement (by way of computer/processor executable instructions) at least one embodiment of the method described in greater detail below that is configured to enhance the binaural representation for hearing-impaired subjects.

Cochlear implant 4A further includes a transmitter 10A which is coupled to and receives the output from processing module 8A. In the exemplary embodiment, transmitter 10A is a coil held in position by a magnet placed behind the external ear, and transmits power and the processed sound signals across the skin to the internal components of cochlear implant 4A described below by electromagnetic induction.

Cochlear implant 4A still further includes a receiver and stimulator module 12A which is secured in bone beneath the skin of the subject. Receiver and stimulator module 12A converts the signals received from transmitter 10A into electric impulses and sends them through an internal cable to electrode array 14A. Electrode array 14A comprises a number of electrodes wound through the cochlea in the scala tympani which send the impulses to the nerves and then directly to the brain through the auditory nerve system.

Finally, cochlear implant 4A includes a short range wireless communications module 16A that is structured and configured to enable cochlear implant 4A to communicate with cochlear implant 4B over a short range wireless network.

As seen in FIG. 2, cochlear implant 4B is similar in structure to cochlear implant 4A and includes microphone(s) 6B, processing module 8B (having processor 7B and memory 9B), transmitter 10B, receiver and stimulator module 12B, electrode array 14B, and short range wireless communications module 16A. These components are similar in structure and function to the corresponding components of cochlear implant 4A described above. Short range wireless communications module 16B is structured and configured to enable cochlear implant 4B to communicate with cochlear implant 4A over a short range wireless network. The significance of this two way communications capability between cochlear implant 4A and cochlear implant 4B is described elsewhere herein.

Figure 3:
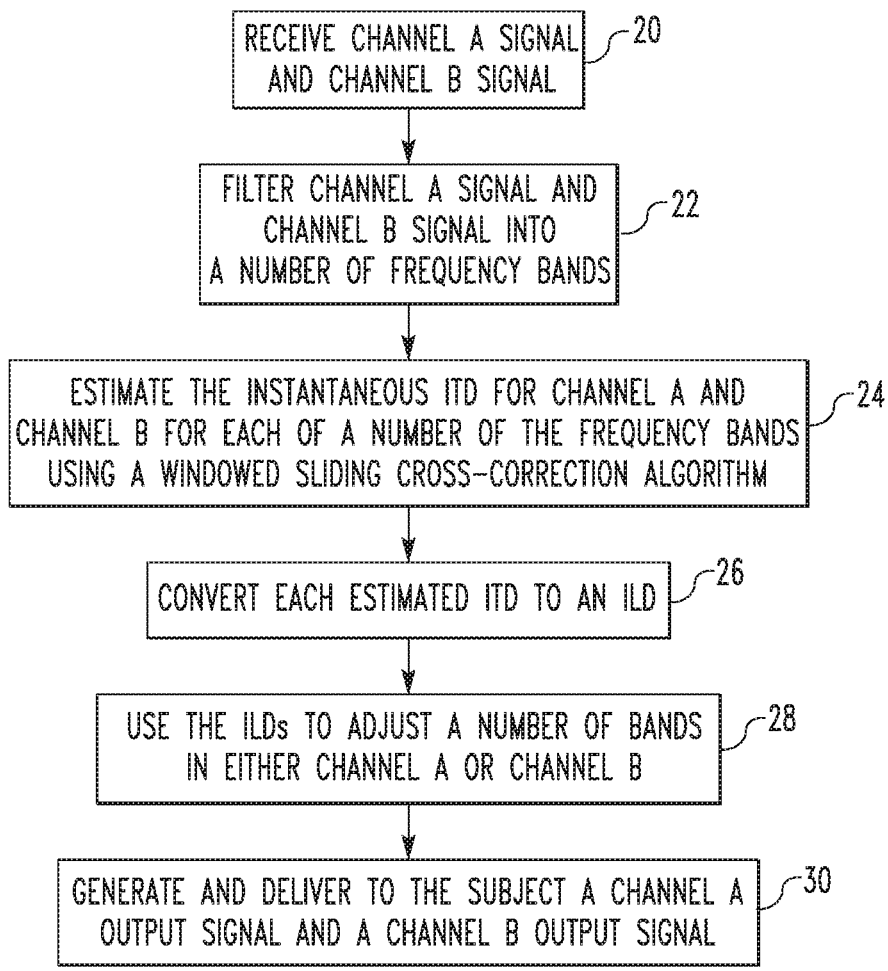
FIG. 3 is a flowchart of a method for enhancing the binaural representation for hearing-impaired subjects according to one exemplary, non-limiting embodiment of the disclosed concept that may be implemented in the system of FIG. 2.

FIG. 3 is a flowchart of a method for enhancing the binaural representation for hearing-impaired subjects according to one exemplary, non-limiting embodiment of the disclosed concept. In the exemplary embodiment described below, the method is described as being implemented in the system of FIG. 2. It will be understood, however, that that is meant to be exemplary only, and that the method may also be implemented in alternative systems designed to assist the hearing impaired, such as systems employing two hearing aids or even, as discussed elsewhere herein, a system employing a single or no hearing enhancement device. In addition, the method of FIG. 3 is designed to be repeated periodically by system 2. In the exemplary embodiment, the method is repeated by system 2 every 20 µs (although it will be appreciated that other repeating time periods are also possible).

Referring to FIG. 3, the system begins at step 20, wherein, in response to a number of sound sources in an auditory scene (such as, for example and without limitation, an auditory scene wherein a target is speaking on one side of the subject and a masker is speaking on the other side of the subject), microphone(s) 6A generates and passes to processing module 8A a first signal (referred to herein as the "channel A signal") and microphone(s) 6B generates and passes to processing module 8B a second signal (referred to herein as the "channel B signal"). Next, at step 22, processing module 8A digitizes the channel A signal and filters it into a number of frequency bands and processing module 8B digitizes the channel B signal and filters it into a number of frequency bands. In the non-limiting exemplary embodiment, each signal is filtered into 32 ERB-wide frequency bands, although it will be appreciated that different numbers and/or sizes of bands may also be used. In the exemplary embodiment, processing module 8B then causes the channel B frequency band data to be transmitted wirelessly to processing module 8A of cochlear implant 4A using wireless communications module 16 B (which communicates with wireless communications module 16A). As a result, processing module 8A will have both the channel A frequency band data and the channel B frequency band data. Thus, in this example, processing module 8A acts as the master and processing module 8B acts as the slave. As will be appreciated, these roles may be reversed, with processing module 8B acting as the master and processing module 8A acting as the slave. In another alternative, the channel B signal in its unfiltered form may be wirelessly transmitted to processing module 8A which then filters it into the number of frequency bands for further processing as described above.

Next, at step 24, processing module 8A estimates the instantaneous ITD for (i.e., between) channel A and channel B for each of a number of the frequency bands. In the exemplary embodiment, processing module 8A employs a windowed sliding cross correlation algorithm to estimate each of the ITDs. In one particular, non-limiting embodiment, the algorithm used a 1.2 ms (±600 µs) window size, and a 22.68 µs step size (1 sample at 44100 kHz). In each window, the between-channel delay that produced the largest correlation is taken as the instantaneous ITD. It will be appreciated, however, that the above is meant to be exemplary only and that alternative techniques/algorithms, such as alternative correlation techniques/algorithms, may be used to estimate the instantaneous ITD for each of the frequency bands. Furthermore, in the exemplary embodiment, the processing module 8A estimates the instantaneous ITD for each of the first 15 of the 32 frequency bands (i.e., frequencies less then or equal to approximately 1500 Hz). Again, this is not meant to be limiting, as other ones of the frequency bands (e.g., the first 20 or all 32) may also be used.

Then, at step 26, each of the estimated ITDs is converted into an ILD based on a predetermined scheme. For example, the scheme may be a formula or a look-up table that converts each ITD value into a corresponding ILD value. In the exemplary embodiment, ±600-µs ITDs are converted to ILDs of ±30 dB, 0-µs ITDs are converted to 0-dB ILDs, and intermediate values are linearly interpolated.

Next, at step 28, each of the determined ILDs is used to adjust the value of the data of the corresponding frequency band of either the channel A frequency band data or the channel B frequency band data. In particular, in the exemplary embodiment, the determined ILDs are applied to the channel A and channel B signals by attenuating the signal (i.e., attenuating the corresponding frequency band data) to the ear (either channel A or channel B) that is contralateral to the apparent location of the sound as estimated by the corresponding ITD. In the exemplary embodiment, positive ITDs and ILDs are applied such that the left channel is attenuated, and negative ITDs and ILDs are applied such that the right channel is attenuated. Thus, for example, if the ITD for a given frequency band at a given moment in time is estimated to be −300 µs (i.e., to the left) (e.g., to channel A), the frequency band for the right ear (e.g., channel B) will be attenuated, for example by 15 dB using the linear interpolation method described above.

There are a number of ways in which step 28 may be accomplished in system 2. For example, once each of the ITDs and ILDs have been determined, processing module 8A may perform the required adjustments to the channel A frequency band data and/or the channel B frequency band data as needed such that adjusted channel A frequency band data and adjusted channel B frequency band data will then exist. The adjusted channel B frequency band data may then be sent wirelessly to processing module 8B for used thereby as described below. Alternatively, processing module 8A may generate and wirelessly transmit instructions to processing module 8B which indicate to processing module 8B what adjustments need to be made to create the adjusted channel B frequency band data in processing module 8B (the adjusted channel A frequency band data will be generated as needed in processing module 8A). Regardless of how this step is done, following step 28, processing module 8A will have the adjusted channel A frequency band data and processing module 8B will have the adjusted channel B frequency band data.

Next, at step 30, processing module 8A sums the adjusted channel A frequency band data to create a channel A output signal and processing module 8B sums the adjusted channel B frequency band data to create a channel B output signal. Those output signals are then provided to transmitter 8A and transmitter 8B, respectively, and operation continues from there as described elsewhere herein to cause appropriate stimulation signals to be delivered to the subject.

The method just described requires no a priori knowledge of the sound sources. A significant limitation to typical noise reduction approaches is that, in the case of two concurrent talkers, the algorithm has no way of knowing which is the target and which is the noise, and only one talker can receive the benefit, to the detriment of the other. The user is not afforded the ability to switch attention from one to the other, as occurs naturally for normal-hearing listeners in natural multiple-talker environments. The described method does not suffer from this limitation. When two talkers are on either side of the mid-saggital plane of the listener, both talkers receive a benefit in SNR from the method presently disclosed, at the near ear. This leaves the listener free to attend to one or the other talker, and even switch attention as he or she likes.

The described method is shown to provide significant benefit to speech understanding in the presence of a competing talker, but it should be beneficial in other types of backgrounds as well, such as steady-state noise. It should also be beneficial with multiple (>2) sound sources.

For hearing impaired listeners who use a single unilateral hearing enhancement device, the potential benefit from the described method may be enough to warrant the use of a second device that would allow the method to be implemented, even if that is the sole purpose of the second device (i.e., amplification may not be required in the subject's ipsilateral ear).

This method has been demonstrated by the present inventor through experimentation to significantly improve speech intelligibility for eight BCI users. Cochlear implant users typically suffer significant declines in speech understanding in the presence of background noise, and often show the largest declines in single-talker backgrounds, a pattern that is also often observed in listeners with hearing impairment. Users of bilateral hearing aids should also benefit, as well as users of unilateral devices (hearing aid or cochlear implant), provided that a contralateral microphone and suitable data link are available. In addition, the disclosed concept should provide significant benefit to users of bilateral hearing aids, even if they already shows good localization abilities and SRM. This is because the technique described herein improves the SNR, which will be beneficial with or without spatial abilities.

Furthermore, there are many listeners whose hearing thresholds are good enough that aids do not provide benefit, but who still show significant performance declines in multiple-talker environments. These declines may be due to presbicusis, or cognitive or attentional deficits. The described method may provide significant benefit in many of these cases via the improved SNR described earlier. In these cases, benefit may be obtained by utilizing the described method with two hearing aids.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A hearing enhancement device, comprising:
   one or more first microphones structured and configured to generate a first signal in response to a plurality of sound sources;
   one or more second microphones structured and configured to generate a second signal in response to the plurality of sound sources; and
   a processing apparatus structured and configured to:
   filter the first signal and the second signal into a plurality of frequency bands;
   responsive to the filtering of the first signal into the plurality of frequency bands, for each of the plurality of frequency bands, estimate an instantaneous binaural cue between the first signal and the second signal using a correlation algorithm, the estimated instantaneous binaural cues being a plurality of estimated binaural cues of a first type;
   responsive to the estimating of the instantaneous binaural cue between the first signal and the second signal for each of the plurality of frequency bands, convert each of the plurality of estimated binaural cues of the first type to a corresponding binaural cue of a second type different than the first type; and
   use one or more of the corresponding binaural cues of the second type to generate an adjusted first signal;
   wherein the hearing enhancement device is structured and configured to use the adjusted first signal to generate a number of signals to be delivered to a subject by the hearing enhancement device for enhancing the hearing of the subject.

2. The hearing enhancement device according to claim 1, wherein the plurality of estimated binaural cues of a first type are a plurality of estimated interaural time differences, and wherein each corresponding binaural cue of a second type different than the first type is a corresponding interaural level difference.

3. The hearing enhancement device according to claim 1, wherein the processing apparatus is structured and configured to se the one or more of the corresponding binaural cues of the second type to generate the adjusted first signal by using each of the corresponding binaural cues of the second type to generate the adjusted first signal.

4. The hearing enhancement device according to claim 3, wherein the hearing enhancement device is structured and configured to use the adjusted first signal and the second signal to generate the number of signals to be delivered to the subject by the hearing enhancement device for enhancing the hearing of the subject.

5. The hearing enhancement device according to claim 1, wherein the hearing enhancement device is a cochlear implant or a hearing aid.

6. The hearing enhancement device according to claim 1, wherein the correlation algorithm is a windowed sliding cross correlation algorithm.

7. The hearing enhancement device according to claim 1, wherein each of the estimated binaural cues of the first type and each of the corresponding binaural cues of the second type is associated with a respective one of the plurality of frequency bands, and wherein the processing apparatus is structured and configured to use the one or more of the corresponding binaural cues of the second type to generate the adjusted first signal by attenuating a value of each of the plurality of frequency bands using the associated corresponding binaural cue of the second type to create a plurality of adjusted frequency bands and summing at least the plurality of adjusted frequency bands to form the adjusted first signal.

8. The hearing enhancement device according to claim 7, wherein the first plurality of frequency bands have a frequency of 1500 Hz or less.

9. The hearing enhancement device according to claim 1, wherein the converting each of the estimated binaural cues of the first type to the corresponding binaural cue of the second type different than the first type employs a predetermined scheme.

10. The hearing enhancement device according to claim 9, wherein the predetermined scheme comprises a look-up table.

11. A hearing enhancement system, comprising:
one or more first microphones structured and configured to generate a first signal in response to a plurality of sound sources;
one or more second microphones structured and configured to generate a second signal in response to the plurality of sound source; and
an apparatus coupled to the one or more first microphones and the one or more second microphones, the apparatus being structured and configured to implement an algorithm, wherein the algorithm is structured and configured to:
filter the first signal and the second signal into a plurality of frequency bands;
responsive to the filtering of the first signal and the second signal into plurality of frequency bands, for each of the plurality of frequency bands, estimate an instantaneous binaural cue between the first signal and the second signal using a correlation algorithm, the estimated instantaneous binaural cues being a plurality of estimated binaural cues of a first type;
responsive to the estimating of the instantaneous binaural cue between the first signal and the second sign for each of the plurality of the frequency bands, a convert each of the plurality of estimated binaural cues of the first type to a corresponding binaural cue of a second type different than the first type; and
use one or more of the corresponding binaural cues of the second type to generate an adjusted first signal;
wherein the system is structured and configured to use the adjusted first signal to generate a number of signals to be delivered to a subject for enhancing the hearing of the subject.

12. The hearing enhancement system according to claim 11, wherein the one or more first microphones and the one or more second microphones are part of a hearing enhancement device, and wherein the hearing enhancement device is structured and configured to generate the number of signals to be delivered to the subject for enhancing the hearing of the subject.

13. The hearing enhancement system according to claim 12, wherein the hearing enhancement device is a cochlear implant or a hearing aid.

14. The hearing enhancement system according to claim 11, wherein the plurality of estimated binaural cues of a first type are a plurality of estimated interaural time differences, and wherein each corresponding binaural cue of a second type different than the first type is a corresponding interaural level difference.

15. The hearing enhancement system according to claim 11, wherein the apparatus is structured and configured to use the one or more of the corresponding binaural cues of the second type to generate the adjusted first signal by using each of the corresponding binaural cues of the second type to generate the adjusted first signal.

16. The hearing enhancement system according to claim 15, wherein the system is structured and configured to use the adjusted first signal and the second signal to generate the number of signals to be delivered to the subject for enhancing the hearing of the subject.

17. The hearing enhancement system according to claim 11, wherein the correlation algorithm is a windowed sliding cross correlation algorithm.

18. The hearing enhancement system according to claim 11, wherein each of the estimated binaural cues of the first type and each of the corresponding binaural cues of the second type is associated with a respective one of the plurality of frequency bands, and wherein the algorithm is structured and configured to use the one or more of the corresponding binaural cues of the second type to generate the adjusted first signal by attenuating a value of each of the plurality of frequency bands using the associated corresponding binaural cue of the second type to create a plurality of adjusted frequency bands and summing at least the plurality of adjusted frequency bands to form the adjusted first signal.

19. The hearing enhancement system according to claim 18, wherein the first plurality of frequency bands have a frequency of 1500 Hz or less.

20. The hearing enhancement system according to claim 11, wherein the converting each of the estimated binaural cues of the first type to the corresponding binaural cue of the second type different than the first type employs a predetermined scheme.

21. The hearing enhancement system according to claim 20, wherein the predetermined scheme comprises a look-up table.

22. A hearing enhancement method, comprising:
generating a first signal in response to a plurality of sound sources;
generating a second signal in response to the plurality of sound sources; and
filtering the first signal and the second signal into a plurality of frequency bands;
responsive to the filtering of the first signal and the second signal into the plurality of frequency bands, for each of the plurality of frequency bands, estimating an instantaneous binaural cue between the first signal and the second signal using a correlation algorithm, the estimated instantaneous binaural cues being a plurality of estimated binaural cues of a first type;
responsive to the estimating of the instantaneous binaural cue between the first signal and the second signal for each of the plurality of frequency bands, converting each of the plurality of estimated binaural cues of the first type to a corresponding binaural cue of a second type different than the first type; and
using one or more of the corresponding binaural cues of the second type to generate an adjusted first signal;
using the adjusted first signal to generate a number of signals to be delivered to a subject by a hearing enhancement device for enhancing the hearing of the subject.

23. The method according to claim 22, wherein each of the estimated binaural cues of the first type and each of the corresponding binaural cues of the second type is associated with a respective one of the plurality of frequency bands, and wherein the method comprises using the one or more of the corresponding binaural cues of the second type to generate the adjusted first signal by attenuating a value of each of the plurality of frequency bands using the associated corresponding binaural cue of the second type to create a plurality of adjusted frequency bands and summing at least the plurality of adjusted frequency bands to form the adjusted first signal.

* * * * *